US009125990B2

(12) United States Patent
Hunter et al.

(10) Patent No.: US 9,125,990 B2
(45) Date of Patent: Sep. 8, 2015

(54) BI-DIRECTIONAL MOTION OF A LORENTZ-FORCE ACTUATED NEEDLE-FREE INJECTOR (NFI)

(75) Inventors: Ian W. Hunter, Lincoln, MA (US); Andrew J. Taberner, Mt. Eden (NZ); N. Catherine Hogan, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 12/960,405

(22) Filed: Dec. 3, 2010

(65) Prior Publication Data

US 2011/0166549 A1    Jul. 7, 2011

Related U.S. Application Data

(63) Continuation of application No. 12/879,787, filed on Sep. 10, 2010, now Pat. No. 8,398,583, which is a continuation-in-part of application No. 12/712,824, filed on Feb. 25, 2010, now abandoned, which is a (Continued)

(51) Int. Cl.
*A61M 5/30* (2006.01)
*A61B 10/00* (2006.01)
(Continued)

(52) U.S. Cl.
CPC .............. *A61M 5/30* (2013.01); *A61B 10/0045* (2013.01); *A61B 10/02* (2013.01); *A61M 5/19* (2013.01);
(Continued)

(58) Field of Classification Search
CPC ... A61B 2017/8838; A61C 5/068; A61J 1/20; A61J 1/2093; A61J 1/2096; A61J 7/0007; A61J 2001/2003; A61M 5/14216; A61M 5/30; A61M 5/31596; A61M 2005/31588; A61M 5/19; A61M 2205/8287; A61M 2005/3128; B01F 5/0685; B01F 11/0071; B01F 11/0074; B01F 13/0023; B01F 15/0279
USPC ...................................... 604/82–92, 518, 520
See application file for complete search history.

(56) References Cited

U.S. PATENT DOCUMENTS 2,194,535 A    3/1940    Von Delden
2,550,053 A    4/1951    Ferguson
(Continued)

FOREIGN PATENT DOCUMENTS

DE    201 05 183 U1    6/2002
DE    101 46 535 A1    4/2003
(Continued)

OTHER PUBLICATIONS

Taberner, A.J., et al., "A Portable Needle-free Jet Injector Based on a Custom High Power-density Voice-coil Actuator," *Proc 28th IEEE EMBS Annual Int'l Conference, USA*, SaBP6.3:5001-5004 (Aug. 30-Sep. 3, 2006).

(Continued)

*Primary Examiner* — Kami A Bosworth
(74) *Attorney, Agent, or Firm* — Hamilton, Brook, Smith & Reynolds, P.C.

(57) ABSTRACT

The present invention relate to a method and corresponding apparatus for just in time mixing of a solid or powdered formulation and its subsequent delivery to a biological body. In some embodiments, a powdered formulation is maintained in a first chamber. A bi-directional electromagnetic actuator is in communication with the chamber. The actuator, when activated, generates a pressure within the first chamber. The pressure results in mixing of the powdered formulation and a diluent in time for delivering into the biological body.

27 Claims, 8 Drawing Sheets

Related U.S. Application Data continuation of application No. 12/459,866, filed on Jul. 8, 2009, now abandoned.

(60) Provisional application No. 61/134,344, filed on Jul. 9, 2008.

(51) Int. Cl.
*A61B 10/02* (2006.01)
*A61M 5/19* (2006.01)
*A61M 5/31* (2006.01)

(52) U.S. Cl.
CPC ....... *A61B 10/0283* (2013.01); *A61B 2010/008* (2013.01); *A61M 2005/3128* (2013.01); *A61M 2205/8287* (2013.01)

(56) References Cited

U.S. PATENT DOCUMENTS

| | | | |
|---|---|---|---|
| 3,057,349 A | 10/1962 | Ismach | |
| 3,788,315 A | 1/1974 | Laurens | |
| 3,923,060 A | 12/1975 | Ellinwood, Jr. | |
| 4,103,684 A | 8/1978 | Ismach | |
| 4,108,177 A | 8/1978 | Pistor | |
| 4,552,559 A | 11/1985 | Donaldson et al. | |
| 4,560,377 A | 12/1985 | Geat et al. | |
| 4,592,742 A | 6/1986 | Landau | |
| 5,074,843 A | 12/1991 | Dalto et al. | |
| 5,116,313 A | 5/1992 | McGregor | |
| 5,347,186 A | 9/1994 | Konotchick | |
| 5,354,273 A | 10/1994 | Hagen | |
| 5,389,085 A | 2/1995 | D'Alessio et al. | |
| 5,405,614 A | 4/1995 | D'Angelo et al. | |
| 5,472,421 A * | 12/1995 | Klearman et al. | 604/82 |
| 5,505,697 A | 4/1996 | McKinnon, Jr. et al. | |
| 5,533,995 A | 7/1996 | Corish et al. | |
| 5,578,495 A | 11/1996 | Wilks | |
| 5,693,016 A | 12/1997 | Gumaste et al. | |
| 5,865,795 A | 2/1999 | Schiff et al. | |
| 5,879,327 A | 3/1999 | Moreau DeFarges et al. | |
| 6,030,399 A | 2/2000 | Ignotz et al. | |
| 6,090,790 A | 7/2000 | Eriksson | |
| 6,203,521 B1 | 3/2001 | Menne et al. | |
| 6,258,062 B1 | 7/2001 | Thielen et al. | |
| 6,939,323 B2 | 9/2005 | Angel et al. | |
| 7,425,204 B2 | 9/2008 | Angel et al. | |
| 7,462,164 B2 * | 12/2008 | Moir | 604/82 |
| 7,530,975 B2 | 5/2009 | Hunter | |
| 7,833,189 B2 | 11/2010 | Hunter et al. | |
| 7,896,849 B2 * | 3/2011 | Delay | 604/181 |
| 8,172,790 B2 | 5/2012 | Hunter et al. | |
| 8,328,755 B2 | 12/2012 | Hunter et al. | |
| 8,398,583 B2 | 3/2013 | Hunter et al. | |
| 8,740,838 B2 | 6/2014 | Hemond et al. | |
| 8,821,434 B2 | 9/2014 | Hunter et al. | |
| 2002/0055729 A1 | 5/2002 | Goll | |
| 2002/0095124 A1 | 7/2002 | Palasis et al. | |
| 2004/0094146 A1 | 5/2004 | Schiewe et al. | |
| 2004/0106893 A1 | 6/2004 | Hunter | |
| 2004/0106894 A1 | 6/2004 | Hunter et al. | |
| 2004/0231667 A1 | 11/2004 | Horton et al. | |
| 2005/0022806 A1 | 2/2005 | Beaumont et al. | |
| 2005/0165358 A1 | 7/2005 | Yeshurun et al. | |
| 2006/0258986 A1 | 11/2006 | Hunter et al. | |
| 2007/0055200 A1 | 3/2007 | Gilbert | |
| 2007/0129693 A1 | 6/2007 | Hunter et al. | |
| 2007/0167907 A1 * | 7/2007 | Deslierres et al. | 604/68 |
| 2008/0009788 A1 | 1/2008 | Hunter et al. | |
| 2008/0139900 A1 | 6/2008 | Randlov et al. | |
| 2009/0012497 A1 * | 1/2009 | Uber et al. | 604/518 |
| 2009/0223513 A1 | 9/2009 | Panania et al. | |
| 2009/0240231 A1 | 9/2009 | Hyde et al. | |
| 2009/0240241 A1 | 9/2009 | Hyde et al. | |
| 2010/0062529 A1 | 3/2010 | Zimmermann et al. | |
| 2010/0140182 A1 | 6/2010 | Chapman et al. | |
| 2011/0082388 A1 | 4/2011 | Hunter et al. | |
| 2011/0311939 A1 | 12/2011 | Hunter | |
| 2012/0095435 A1 | 4/2012 | Hunter et al. | |
| 2013/0102957 A1 | 4/2013 | Hunter et al. | |
| 2015/0005701 A1 | 1/2015 | Hunter et al. | |
| 2015/0025505 A1 | 1/2015 | Hunter et al. | |

FOREIGN PATENT DOCUMENTS

| | | |
|---|---|---|
| EP | 0 834 330 A2 | 4/1998 |
| EP | 1 020 200 A2 | 7/2000 |
| GB | 756957 | 9/1956 |
| JP | 2005-087722 A | 7/2005 |
| WO | WO 2004/022244 | 3/2004 |
| WO | WO 2004/093818 A | 4/2004 |
| WO | WO 2004/112871 A | 12/2004 |
| WO | WO 2006/086774 A | 8/2006 |
| WO | WO 2008/027579 A1 | 3/2008 |

OTHER PUBLICATIONS

"Antares Pharma :: Home; Products; and Injector Technologies" [online, retrieved on Jul. 18, 2011]. Retrieved from the Internet URL: http://www.antarespharma.com.

"Carousel Medical Systems, Inc. Laboratory and Hospital Solutions," [online, retrieved on Jul. 18, 2011]. Retrieved from the Internet URL: http://www.carouselmed.com.

"Needle Free Injection Systems—Crossject Medical Technology," [online, retrieved on Jul. 18, 2011]. Retrieved from the Internet URL: http://www.crossject.com.

"Bioject—Needle-Free Injection Technology," [online, retrieved on Jul. 18, 2011]. Retrieved from the Internet URL: http://www.bioject.com.

"Insulinjet," [online, retrieved on Jul. 18, 2011]. Retrieved from the Internet URL: http://www.insulinjet.com.

"J-Tip—Needle Free Injection System," [online, retrieved on Jul. 18, 2011]. Retrieved from the Internet URL: http://www.jtip.com.

"PenJet® Needle-Less, Disposable Jet Injectors," [online, retrieved on Jul. 18, 2011]. Retrieved from the Internet URL: http://www.penjet.com.

"Valeritas—Delivering Quality of Life," [online, retrieved on Jul. 18, 2011]. Retrieved from the Internet URL: http://www.valeritas.com/mini-ject.shtml.

"Zogenix—Home," [online, retrieved on Jul. 18, 2011]. Retrieved from the Internet URL: http://www.zogenix.com.

"World Leader in Blood Safety for the Transfusion Industry—Novartis Diagnostics," [online, retrieved on Jul. 18, 2011]. Retrieved from the Internet URL: http://www.novartisdiagnostics.com.

"Injex—The Soft Shot," [online, retrieved on Jul. 18, 2011]. Retrieved from the Internet URL: http://www.injex.com.

Notice of Allowance in U.S. Appl. No. 12/879,787, mailed on Nov. 14, 2012.

U.S. Appl. No. 14/504,903, entitled "Bi-Directional Motion of a Lorentz-Force Actuated Needle-Free Injector (NFI)," filed Oct. 2, 2014.

* cited by examiner

FIG. 8A  FIG. 8B

BI-DIRECTIONAL MOTION OF A LORENTZ-FORCE ACTUATED NEEDLE-FREE INJECTOR (NFI)

RELATED APPLICATIONS

This application is a continuation of U.S. application Ser. No. 12/879,787, filed Sep. 10, 2010, which is a continuation-in-part of U.S. application Ser. No. 12/712,824, filed Feb. 25, 2010, which is a continuation of U.S. application Ser. No. 12/459,866, filed Jul. 8, 2009, which claims the benefit of U.S. Provisional Application No. 61/134,344, filed on Jul. 9, 2008.

The entire teachings of the above applications are incorporated herein by reference.

BACKGROUND OF THE INVENTION

Needle-free injection represents an alternative route for drug administration that is free of many of the problems associated with the use of needles (AntaresPharma 2005; Balzer et al. 2001). Needle-free injectors (NFIs) operate by creating a high pressure jet of fluid/powder that penetrates the skin. Delivery is rapid (typically <0.5 s) which reduces apprehension while enhancing patient acceptance and ultimately compliance. In addition, NFIs have been shown to improve the efficacy of certain medications (Taylor et al. 1981; Jackson et al. 2001; Williams et al. 2000). Current NFI injectors use springs or compressed inert gases to propel fluid through the skin and into the underlying tissue. This affords minimal control over the pressure applied to the drug during the time course of the injection, parameters shown to be integral to determining the depth and dispersion of drug delivered (Wendell et al. 2006; Shergold et al. 2006), and hence its absorption into the circulation. Others have incorporated some pressure pulse shaping by using variable orifice gas valves or fast/slow pyrotechnic charges. More recently, Stachowiak et al. (2009) have used piezoelectric actuators for dynamic control of delivery, accomplished at the expense of a limited piston stroke and volume of fluid delivered.

An alternative approach to jet drug delivery is to store energy in electrical form and impose a time varying pressure profile (waveform) on the drug volume through the use of a monitored and servo-controlled electromechanical actuator such as a linear Lorentz force actuator. A moving coil Lorentz-force actuated NFI has been developed (U.S. application Ser. No. 11/354,279, filed Feb. 13, 2006 and published as U.S. Patent Publication No. 2007/0191758, the entire teachings of which are incorporated by reference herein). The inherent bi-directionality of the actuator allows the applied pressure to be controlled and even reversed when necessary.

SUMMARY

An example embodiment of the present invention relates to a method and corresponding apparatus for extraction of a sample from a sample source. The claimed method and apparatus relates to injecting a fluid into the sample source, vibrating the sample source and withdrawing a sample from the sample source, and evaluating the sample source as a function of measuring one or more identifying parameters in the withdrawn sample.

The example embodiment may employ a bi-directional needle-free injector to inject the fluid and withdraw the samples. The sample source may include tissue of a biological body. The injected fluid may be physiological saline. The withdrawn sample may be an extracellular fluid. The one or more identifying parameters may include metabolic or proteomic parameters.

The example embodiment may employ a dual actuated bi-directional needle-free injector to aspirate fluid from a medication vial or tissue or deliver fluid from one of two compartments within the device, subsequent mixing/reconstitution of the sample followed by injection of drug into a biological body.

Another example embodiment of the present invention relates to a method and corresponding apparatus for delivering formulation to a biological body. The apparatus includes a plurality of chambers and a plurality of electromagnetic actuators in communication with the plurality of chambers. The plural chambers include a first chamber for holding a powdered formulation. The electromagnetic actuators, when activated, generate a pressure within at least one chamber of the plurality of chambers that results in mixing of the powdered formulation and a diluent in time for delivering into the biological body.

The plurality of chambers may include a second chamber for holding the diluent for mixing with the powdered formulation.

Certain embodiments may include at least one valve connected to the plural chambers. For example, the at least one valve may include at least two ports, a first port for passing the powdered formulation into the first chamber and a second port for passing the diluent into the second chamber. Certain embodiments may further include a nozzle in fluid communication with the third port. The nozzle may be configured to deliver the resulting mixture near the distal end thereof into the biological body.

In certain embodiments, the plurality of actuators, upon activation in a reverse direction, may aspirate a diluent into at least one chamber of the plurality of chambers. At least one actuator of the plurality of electromagnetic actuators may aspirate the diluent from at least one of a medication vial or a skin of a biological body following delivery of fluid.

Certain embodiments may include at least one valve having a fluid path to a fluid source. The valve, upon being opened, may deliver the diluent for mixing with the powdered drug.

In certain embodiments the plurality of actuators, upon actuation, may oscillate the contents of at least one chamber of the plurality of chambers, resulting in mixing of the powdered formulation and the diluent in time for delivering into the biological body. The actuators, upon actuation, may deliver a mixture resulting from mixing of the powdered formulation and the diluent into the biological body. The actuator may be actuated using a preprogrammed waveform to deliver the mixed drug into the biological body. In certain embodiments, the first chamber may hold the diluent and the powdered formulation such that they are separated by an air gap. Certain embodiments may include a sensor that monitors displacement and volume of the powdered drug and the diluent in relation to the air gap.

In certain embodiments, a reservoir may be connected to the plurality of chambers by at least one valve. The valve, when opened, may allow pressurized diluent to flow into the first chamber through the powdered formulation, resulting in fluidization of the powered formulation in time for delivering into the biological body The diluent may be gas (such as hydrogen gas), water, or physiological saline.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION

A description of example embodiments of the invention follows.

This invention is related to articles and methods for injecting a substance into an animal body. Needle-free injectors and actuators are described in U.S. application Ser. No. 10/200,574, filed Jul. 19, 2002, which issued on Sep. 6, 2005 as U.S. Pat. No. 6,939,323, which claims the benefit of U.S. Provisional Application No. 60/338,169, filed Oct. 26, 2001; U.S. application Ser. No. 10/657,734, filed Sep. 8, 2003, which is a Continuation of U.S. application Ser. No. 10/656,806 filed Sep. 5, 2003, which claims the benefit of U.S. Provisional Application Nos. 60/409,090, filed Sep. 6, 2002 and 60/424,114, filed Nov. 5, 2002; U.S. application Ser. No. 10/657,724, filed Sep. 8, 2003 which is a Continuation of U.S. application Ser. No. 10/656,806 filed Sep. 5, 2003 which claims the benefit of U.S. Provisional Application Nos. 60/409,090, filed Sep. 6, 2002 and 60/424,114, filed Nov. 5, 2002; U.S. application Ser. No. 11/352,916 filed Feb. 10, 2006, which claims the benefit of U.S. Provisional Application 60/652,483 filed Feb. 11, 2005; U.S. application Ser. No. 11/354,279 filed Feb. 13, 2006, which is a Continuation of U.S. application Ser. No. 11/352,916 filed Feb. 10, 2006 which claims the benefit of U.S. Provisional Application No. 60/652,483, filed on Feb. 11, 2005; U.S. application Ser. No. 11/351,887 filed Feb. 10, 2006 which claims the benefit of U.S. Provisional Application No. 60/652,483 filed on Feb. 11, 2005; U.S. Provisional Application 60/735,713 filed Nov. 11, 2005; U.S. application Ser. No. 11/598,556, filed on Nov. 13, 2006, which claims the benefit of U.S. Provisional Application No. 60/735,713, filed on Nov. 11, 2005; U.S. application Ser. No. 11/117,082, filed on Apr. 28, 2005, which is a continuation of U.S. application Ser. No. 10/200,574, filed on Jul. 19, 2002, which is now issued as U.S. Pat. No. 6,939,323, and International Application No. PCT/US2007/019247, filed on Aug. 31, 2007, which claims the benefit of U.S. Provisional Application No. 60/841,794, filed on Sep. 1, 2006.

Further needle-free injectors and Lorentz-Force actuators are described in an article, Taberner, A. J., Ball, N., Hogan, N. C., Hunter, I. W., "A portable Needle-free Jet Injector Based on a Custom High Power-Density Voice-coil Actuator," Proceedings of the 28th Annual International Conference of the IEEE EMBS, New York, N.Y., USA, August 2006, 5001-5004.

The entire teachings of the above applications and articles are incorporated herein by reference.

An example embodiment of the present invention relates to a method and corresponding apparatus that employs a needle-free injector (NFI) for the extraction of sample from sources (e.g. tissue) following delivery of fluid (e.g., physiological saline) using said device. Fluid is injected into the sample source (for example the tissue), followed by vibration of the tissue using the tip of the ampule to promote mixing and finally removal of extracellular fluid in order to measure one or more metabolic or proteomic parameters. This technology would use the bi-directional capability of the NFI and is dependent in part on the principles listed below:

a. Loading, delivery, and reloading of the ampule. Fluid can be loaded into the ampule by reversing the polarity on the amplifier which in turn reverses the motion of the moving coil or voice coil causing it to move backwards retracting the piston. Fluid is fired from the ampule by reversing the polarity again causing the moving coil or voice coil and by extension the piston to move forward after which it can be re-loaded and the cycle repeated.

b. Use of a probe screwed into the front plate to measure skin impedance. Impedance characteristics of biological soft tissues are obtained by touching tissues with a small, hard, vibrating probe and measuring the force response. Given the ease with which the face plate holding the ampule can be modified/interchanged, a probe could be attached to the face plate and the moving coil or voice coil pulsed through a range of frequencies while measuring the force response. This information would be used to evaluate and/or choose an optimal patient-specific waveform for delivery of fluid/drug using a disposable commercially-available ampule of ~300 uL (e.g. the INJEX™ ampule, part #100100).

c. Use of the actuator to measure the viscoelastic properties of the skin at the injection site immediately after injection of a small volume of fluid (e.g. physiological saline). Fluid remaining in the ampule is used to perturb the tissue by pulsing the coil through a range of frequencies as described in item "a."

d. Use of a dual actuated device for just in time mixing of a powder formulation followed by delivery.

e. Use of a dual actuated device for delivery of larger therapeutic drugs at low pressure via a preexisting hole. One of the two actuators delivers a small volume of fluid (e.g. physiological saline) at a velocity sufficient to penetrate the tissue followed by mixing of the remaining fluid with the therapeutic and subsequent delivery of said therapeutic through the hole created by the first injection.

Figure 1:
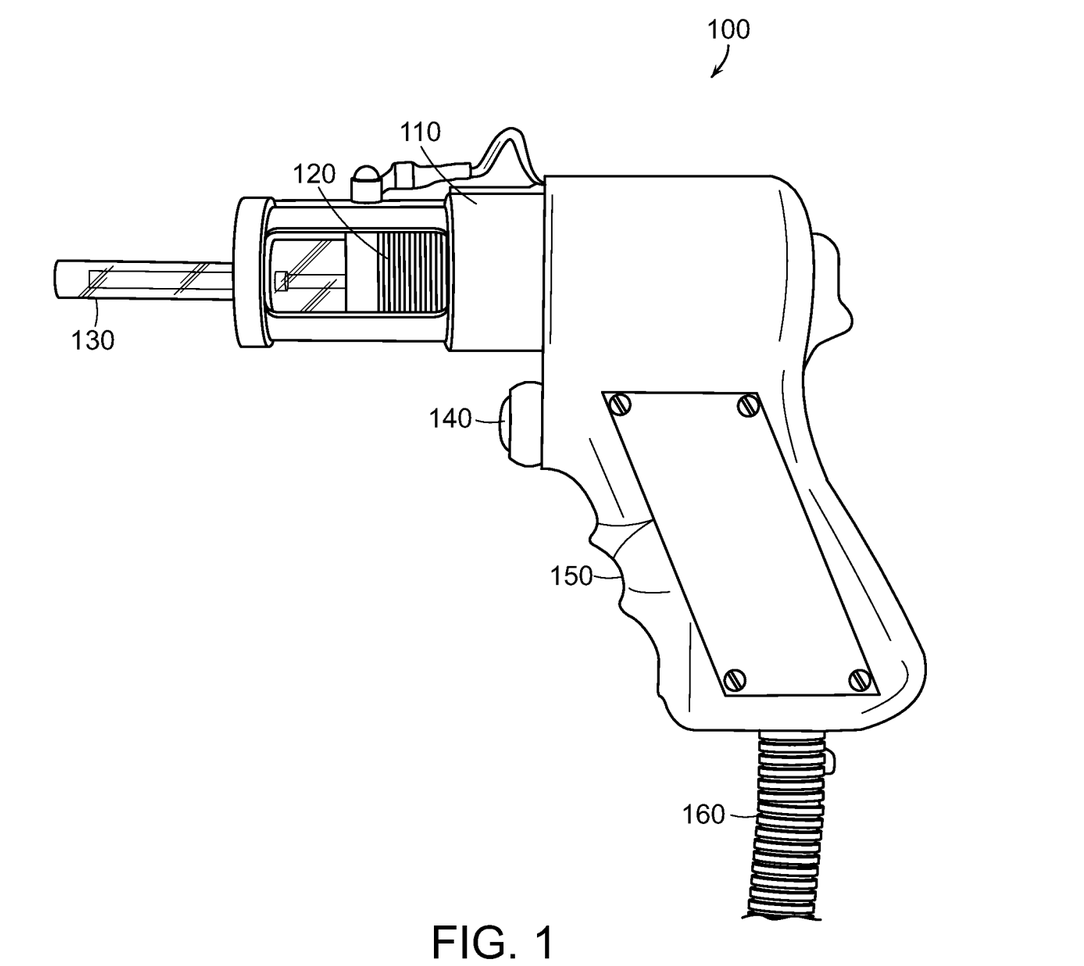
FIG. 1 illustrates a handheld needle free injector that may be used in an example embodiment of the present invention.

FIG. 1 illustrates a handheld NFI 100 that may be used in an example embodiment of the present invention. The NFI 100 includes a disposable commercially available 300 μL NFI INJEX™ ampule 130 attached to a custom designed moving-coil Lorentz force actuator 110. The ampule 130 is screwed into the front plate on the device and the piston is held by a snap-fitting on the front of the moving coil or voice coil 120. The design of the front plate can be easily adapted to accept other ampules. The inherent bi-directionality of the moving-coil 120 allows drug to be easily loaded into the ampule 130 prior to expulsion from the orifice. In certain embodiments, the orifice may have a diameter of 165 μm or 221 μm and a piston diameter of 3.57 mm. The diameter of both the orifice and piston can be varied dependent on the drug and/or volume of drug being delivered.

In certain embodiments, the moving coil or voice coil 120 may include 582 turns of 360 μm diameter polyvinyl butyral coated copper wire wound six layers deep on a thin-walled Acetal copolymer former. This minimizes the moving mass to approximately 50 g and avoids the drag caused by induced eddy currents in a conducting former. The moving coil or voice coil 120 slides on the inside of a 1026 carbon-steel extrusion that also forms the magnetic circuit. The latter consists of two 0.4 MN/m$^2$ (50 MGOe) NdFeB magnets 225 inserted into the casing (Taberner et al. 2006).

The handheld NFI may further include an activation switch 140 that is used to activate the NFI, switch the NFI between ON/OFF positions, and/or activate the Lorentz force actuator. In certain embodiments, the activation switch may function as a safety feature that is used to turn the device on before each use.

In certain embodiments, the NFI may further include a housing 150 that surrounds the interior components of the injector. The NFI may further be coupled with wires 160 that connect to a controller (not shown) that controls various characteristics of the injections. For example, the controller may control various features (e.g., direction) of the moving coil or voice coil actuator 110, injection characteristics such as pressure profile, speed, and etc.

Figure 2:
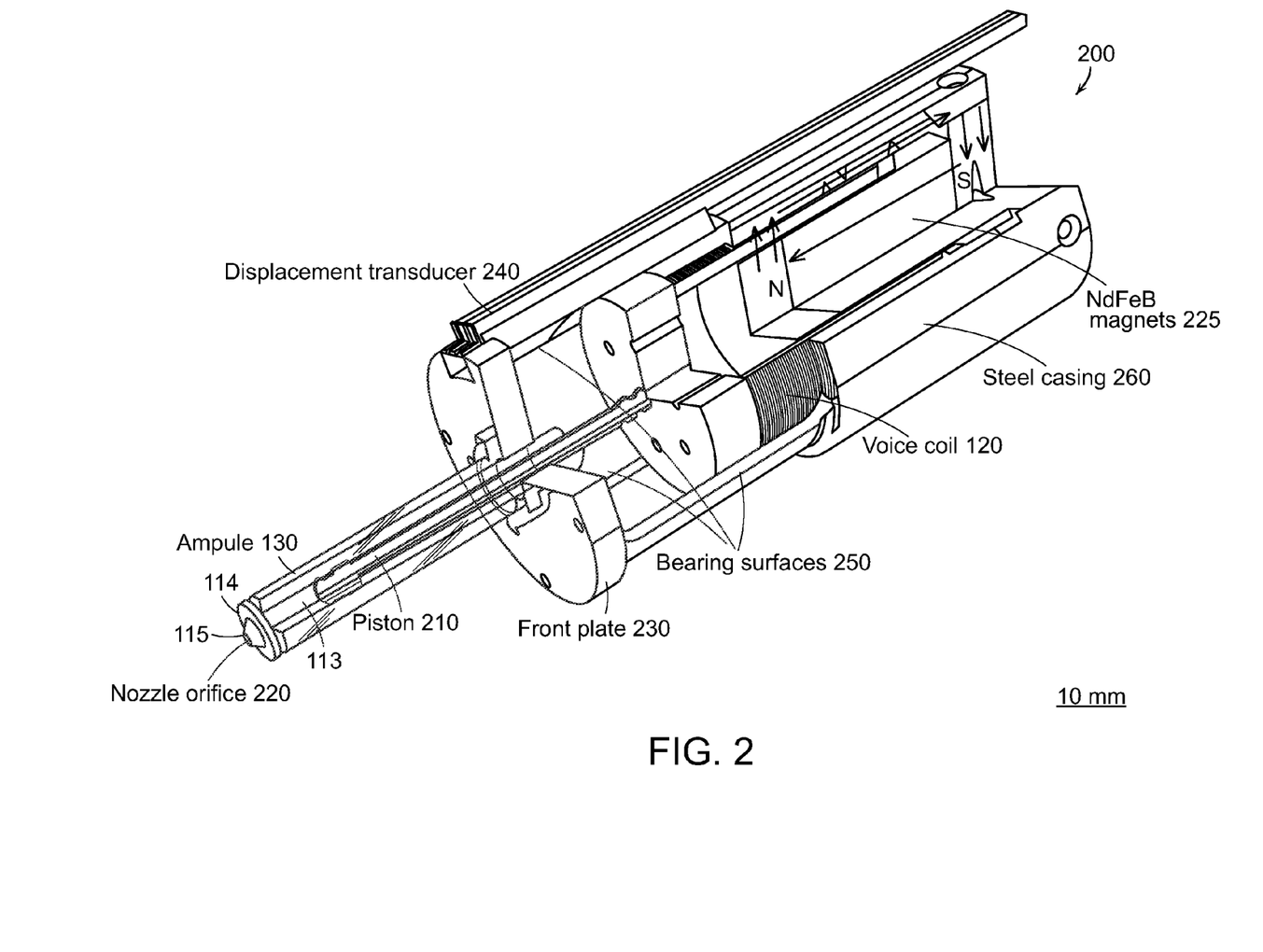
FIG. 2 is an illustration of a cut-away view of the linear actuator of a handheld needle free injector that may be used in an example embodiment of the present invention.

FIG. 2 is a cut-away view of the linear actuator 110 of a handheld needle free injector 200 that may be used in an example embodiment of the present invention.

In this embodiment, plastic-laminated, flexible copper ribbons form the electrical connections to the moving coil or voice coil 120. A linear potentiometer (not shown) mounted to a linear guide system (not shown) monitors the position of the moving coil or voice coil 120. In certain embodiments the moving coil or voice coil 120 may operate at a bandwidth of more than 1 kHz. The position sensor (not shown) may be coupled to the voice coil 120 via a movable pin that is mounted on the leading edge of the former. In certain embodiments, the system may be powered by a 4 kW Techron amplifier, controlled by a PC-based data acquisition and control system running in National Instruments LABVIEW™ 8.5 (Taberner et al. 2006).

The NFI may include an injection ampule 130. In some embodiments, the NFI may further include a nozzle to convey the substance through the surface of the biological body at the required speed and diameter to penetrate the surface (e.g., skin). The nozzle generally contains a flat surface, such as the head 115 that can be placed against the skin and an orifice 220. The nozzle 114 may be coupled to a syringe (not shown) or ampule 130 defining a reservoir 113 for temporarily storing the transferred substance. The syringe or ampule also includes a plunger or piston 210 having at least a distal end slidably disposed within the reservoir. Movement of the plunger 210 along the longitudinal axis of the syringe or ampule 130 in either direction creates a corresponding pressure within the reservoir. As shown in FIG. 2, the NFI includes front plate 230 and bearing surfaces 250.

The linear actuator 110 may further include a magnet assembly 225 that includes a column of magnets disposed along a central axis. The column of magnets can be created by stacking one or more magnetic devices. For example, the magnetic devices can be permanent magnets. As a greater magnetic field will produce a greater mechanical force in the same coil, thus stronger magnets are preferred. As portability and ease of manipulation are important features for a handheld device 100, high-density magnets are preferred.

One such category of magnets are referred to as rare-earth magnets, also know as Neodymium-Iron-Boron magnets (e.g., $Nd_2Fe_{14}B$). Magnets in this family are very strong in comparison to their mass. Currently available devices are graded in strength from about N24 to about N54—the number after the N representing the magnetic energy product, in megagauss-oersteds (MGOe). In one particular embodiment, N50 magnets are used.

The magnets are attached at one end of a casing 260 defining a hollowed axial cavity and closed at one end. The casing 260 is preferably formed from a material adapted to promote containment therein of the magnetic fields produced by the magnets. For example, the casing 260 may be formed from a ferromagnetic material or a ferrite. One such ferromagnetic material includes an alloy referred to as carbon steel (e.g., American Iron and Steel Institute (AISI) 1026 carbon steel).

In certain embodiments, the biological surface is stretched prior to transfer of the substance. First stretching the surface or skin permits the skin to be pierced using a lower force than would otherwise be required. Stretching may be accomplished by simply pressing the nozzle into the surface of the skin. In some embodiments, a separate surface reference or transducer 240 is included to determine when the surface has been sufficiently stretched prior to transfer. Such a sensor can also be coupled to a controller, prohibiting transfer until the preferred surface properties are achieved.

Figure 3:
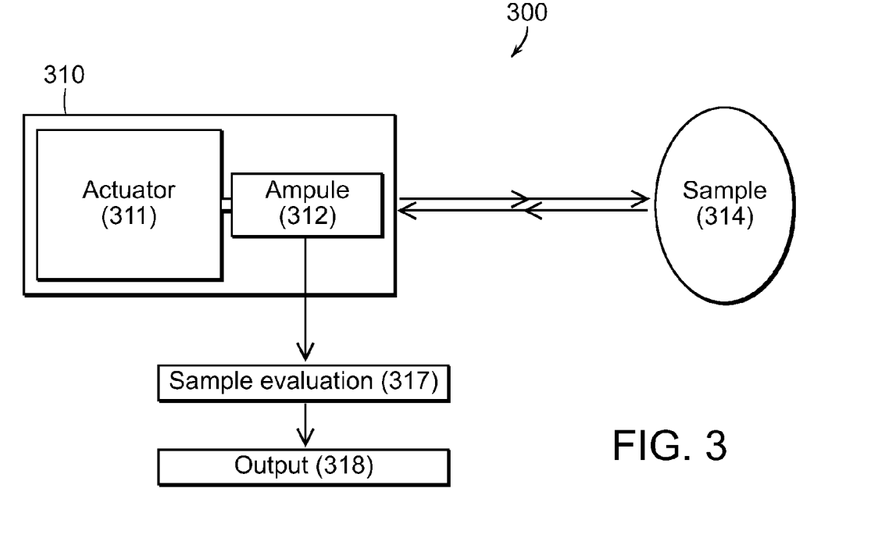
FIG. 3 is a high level illustration of an apparatus for extraction of a sample from a sample source according to an example embodiment of the present invention.

In some embodiments, the NFI includes a transducer 240, such as a displacement sensor used to indicate location of an object's coordinates (e.g., the coil's position) with respect to a selected reference. Similarly, a displacement may be used to indicate movement from one position to another for a specific distance. For example, the sensed parameter can be used as an indication of a change in the coil (120) position and hence the piston tip/plunger's (210) position. By extension this provides an indication of the volume or dose delivered. In some embodiments, as defined in the above example, a proximity sensor may be used to indicate when a portion of the device, such as the coil, has reached a critical distance. Other types of sensors suitable for measuring position or displacement could include inductive transducers, resistive sliding-contact transducers, photodiodes, and linear-variable-displacement-transformers (LVDT). FIG. 3 is a high level illustration of the system used for extraction of a sample from a sample source according to an example embodiment of the present invention.

In this example embodiment 300, a bi-directional needle-free injection system 310 injects a fluid into the sample source (e.g., a biological body such as skin). The sample source is vibrated using the tip of the ampule 312 or a probe screwed into the front plate of the actuator 311 in place of the ampule by actuation of the moving coil or voice coil. The motion of the actuator is then reversed and the sample is removed from the sample source 314. The sample may be extracellular fluid. A sample evaluation module 317 evaluates the sample source as a function of measuring one or more identifying parameters in the withdrawn sample and outputs the evaluation results 318. The one or more identifying parameters may include metabolic or proteomic parameters.

Figure 4:
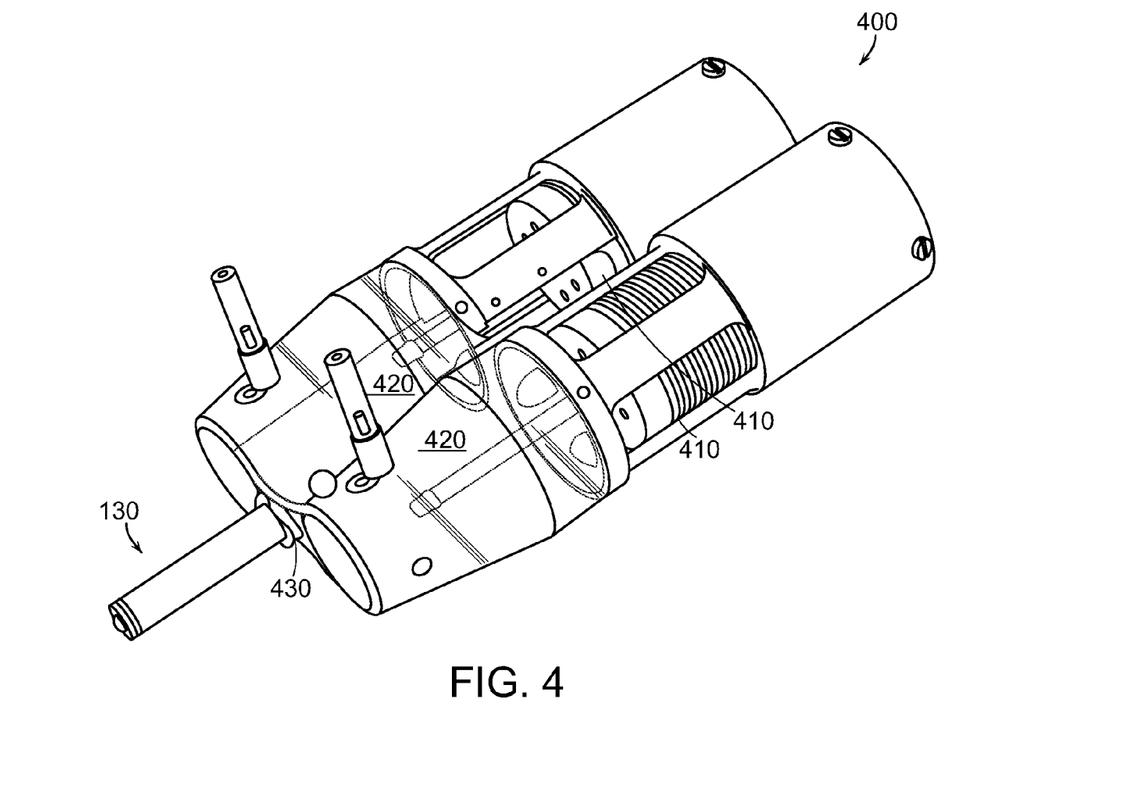
FIG. 4 is a computer-aided design (CAD) drawing of a dual-actuated needle-free injector.

FIG. 4 is a computer-aided design (CAD) drawing of a dual-actuated needle-free injector 400 that may be used in an example embodiment of the present invention. In this example embodiment, fluid (e.g., physiological saline) is delivered to the sample source (e.g., a biological body such as tissue) by one of two actuators 410. The sample may be vibrated using the tip of the ampule 130 prior to aspiration of fluid (e.g., extracellular fluid) from the sample injection site into the second of two reservoirs 420 where it may be used to reconstitute analytic components (e.g., enzyme, buffer, substrate) contained within the second reservoir and required for subsequent evaluation of the sample.

In certain embodiments, one of the two actuators 410 may be used to deliver an incremental volume of fluid (e.g., physiological saline aspirated from a medication vial or pre-filled) at a pressure, monitored by a pressure transducer 430, sufficient to penetrate the sample source followed by mixing of the remaining fluid with a therapeutic held in the second reservoir. Reconstitution or mixing of the therapeutic using the dual actuated system would be followed by delivery through the hole created by the first injection.

Figure 5A:
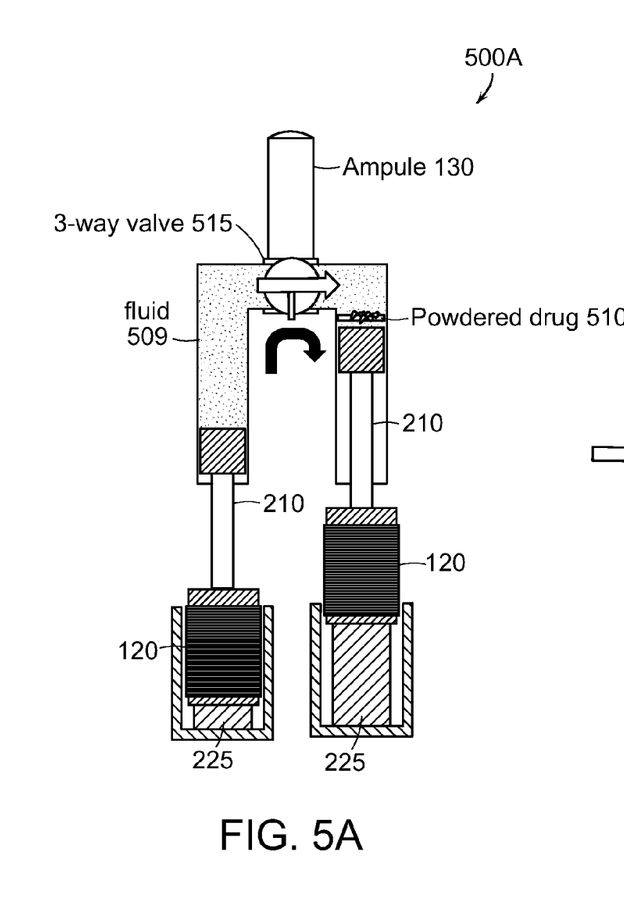
FIG. 5A-5B are schematics illustrating just in time mixing of a solid/powdered formulation (e.g., drug) using a dual actuated needle-free injector.
Figure 5B:
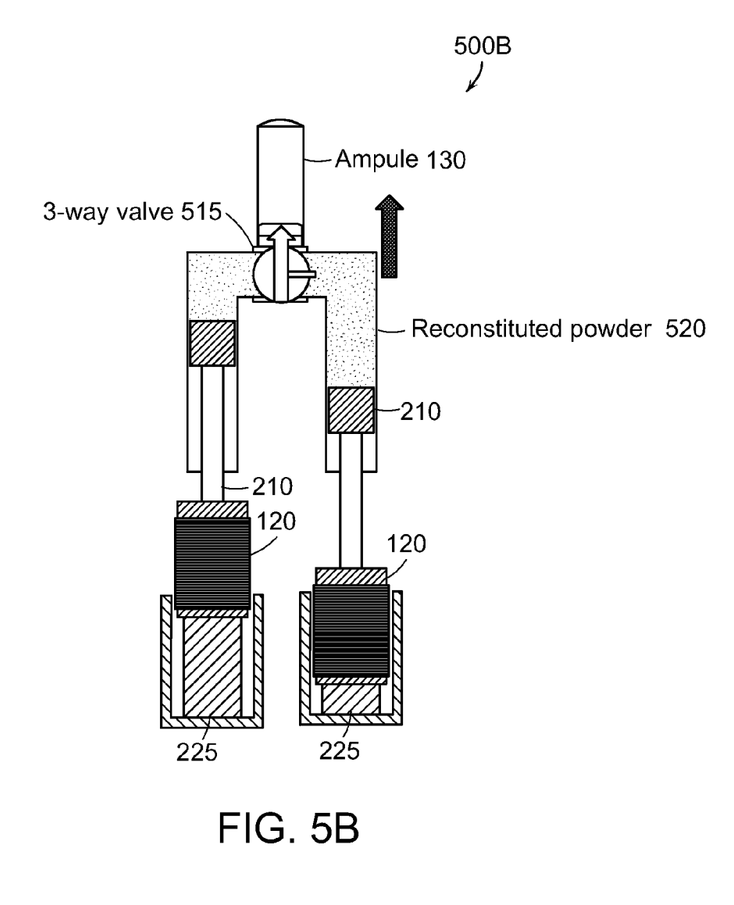

FIGS. 5A-5B are schematics 500A, 500B illustrating just in time mixing of a solid/powdered formulation (e.g., drug) using a dual actuated needle-free injector. As shown in FIG. 5A, fluid 509 and powdered drug 510, each contained within a separate chamber are mixed by dual actuation using a three port valve 515. As shown in FIG. 5B, once mixed (shown as reconstituted powder 520), the valve is adjusted such that the drug is delivered using one of the two actuators via an attached ampule 130 to the biological body. Electromagnetic actuators 225 may be used in mixing of the fluid and the powdered drug. As shown in FIGS. 5A-5B, the moving coil or voice coils 120 may generate a pressure that results in mixing of the powdered drug/formulation and the diluent fluid in time for delivering into the biological body.

Figure 6:
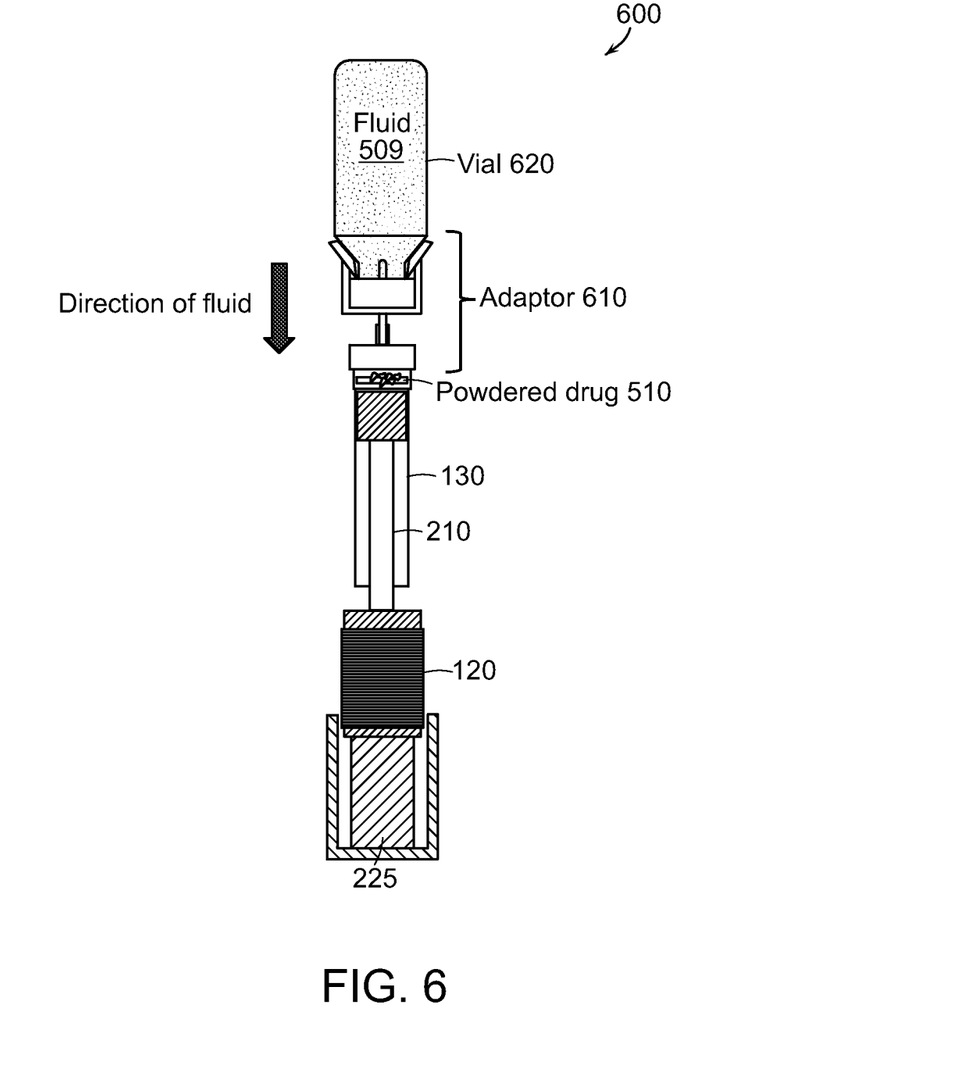
FIG. 6 is a schematic illustrating aspiration of fluid into the drug retention chamber by reversal of the actuator and therefore the piston which is contiguous with the actuator to achieve just in time mixing.

FIG. 6 is a schematic 600 illustrating aspiration of fluid 509 into the drug retention chamber by reversal of the moving coil or voice coil 120 and therefore the piston 210 which is contiguous with the actuator to achieve just in time mixing. As shown in FIG. 6, fluid 509 is aspirated (for example, from vial 620 or from a biological body (not shown)) into the drug retention chamber/ampule 130 by reversing the linear Lorentz-force actuator 120 and therefore the piston 210. Further mixing of the powdered drug 510 and the fluid 509 is achieved by oscillation of the moving coil or voice coil 120 and by extension of the piston 210 within a narrow voltage. Alternatively, mixing of the powdered drug 510 and the fluid 509 may be achieved using an ultrasonic transducer (not shown) incorporated into the piston assembly. Once reconstituted, the appropriate volume of drug is ejected from the ampule 130 by actuation of the moving coil or voice coil 120 using a preprogrammed waveform. An adapter 610 may be used to connect the vial to the NFI.

Figure 7A:
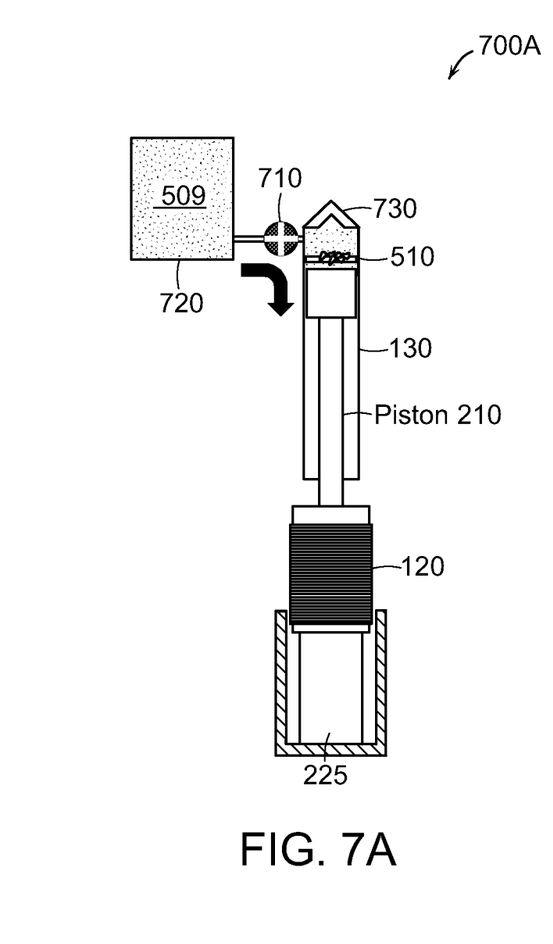
FIG. 7A-7B are schematics showing reconstitution of powdered drug via an independent fluid path or channel.
Figure 7B:
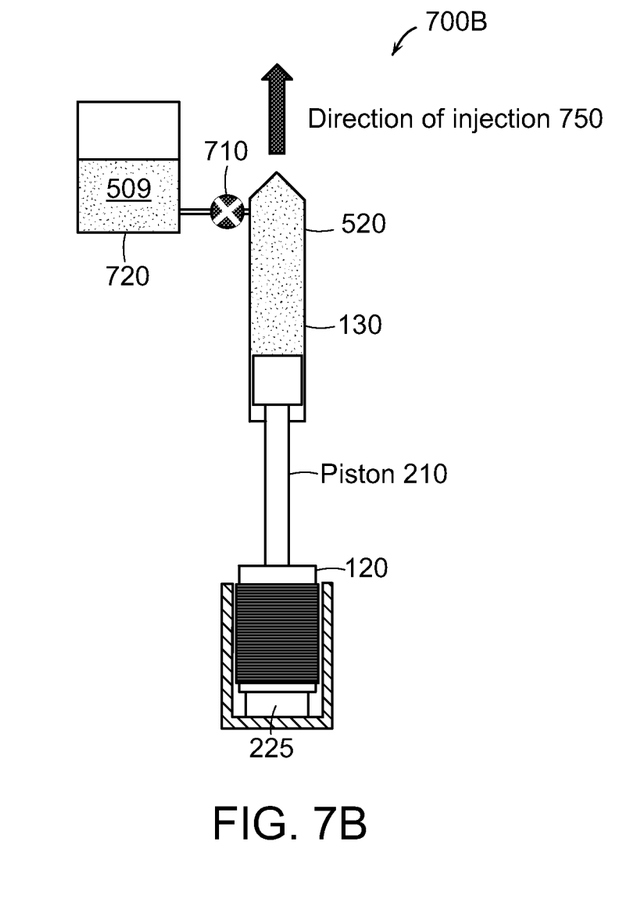

FIGS. 7A-7B are schematics 700A-700B showing reconstitution of powdered drug 510 via an independent fluid path or channel. Diluent 509 may be delivered to the chamber containing powdered drug 510 via an independent fluid path or channel using a valve 710 located at the proximal end of the ampule 130. Closure of the valve 710 after delivery of the desired volume would seal the channel from the drug reservoir 720. The drug reservoir 720 may be oscillated by actuation of the moving coil or voice coil 120 using the electromagnetic actuators 225. The reconstituted drug 520 (shown in FIG. 7B) is then delivered to a biological body through the nozzle 130 (initially covered by nozzle cap 730) in the direction of injection 750.

Figure 8A:
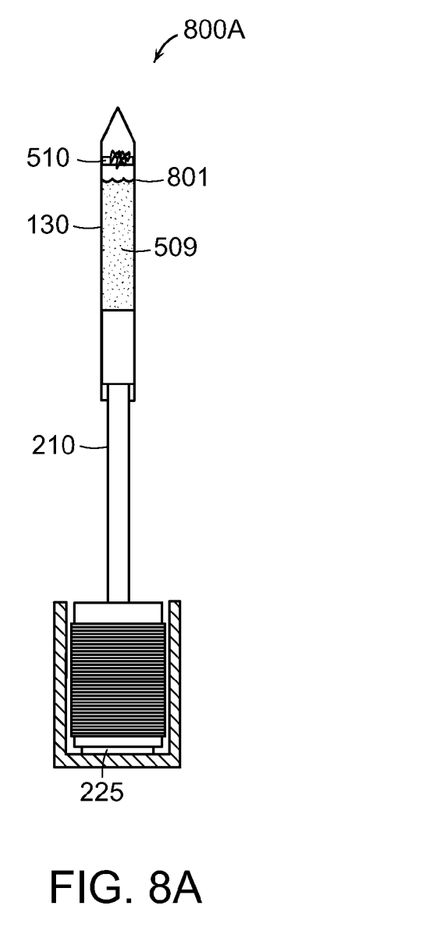
FIG. 8A-8B are schematics illustrating mixing of powdered drug and fluid separated by an air gap.
Figure 8B:
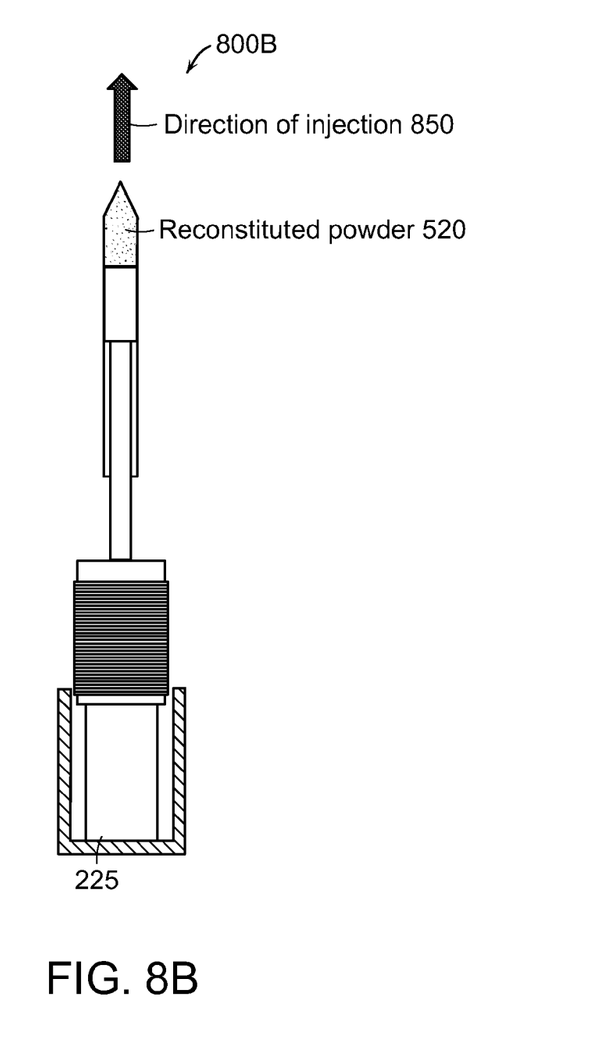

FIGS. 8A-8B are schematics 800A, 800B illustrating mixing of powdered drug 510 and fluid 509 separated by an air gap. In certain embodiments, the powdered drug 510 and fluid 509 may be separated by an air gap 801 in a single cassette. A sensor (not shown) may be utilized to monitor displacement, the change in stroke, as defined by the fluid volume in the chamber. Upon actuation of the electromagnetic actuator 225, the piston 210 drives the fluid volume into the powder 510 resulting in mixing of the powder 510 and fluid 509 (which could be amplified by oscillation of the piston 210). Air could be purged from the chamber in a manner comparable to removing air from a conventional syringe after which the reconstituted drug could be ejected through the ampule 130 and the nozzle (shown in FIGS. 7A-7B) orifice by a second actuation in the direction of injection 850.

Figure 9A:
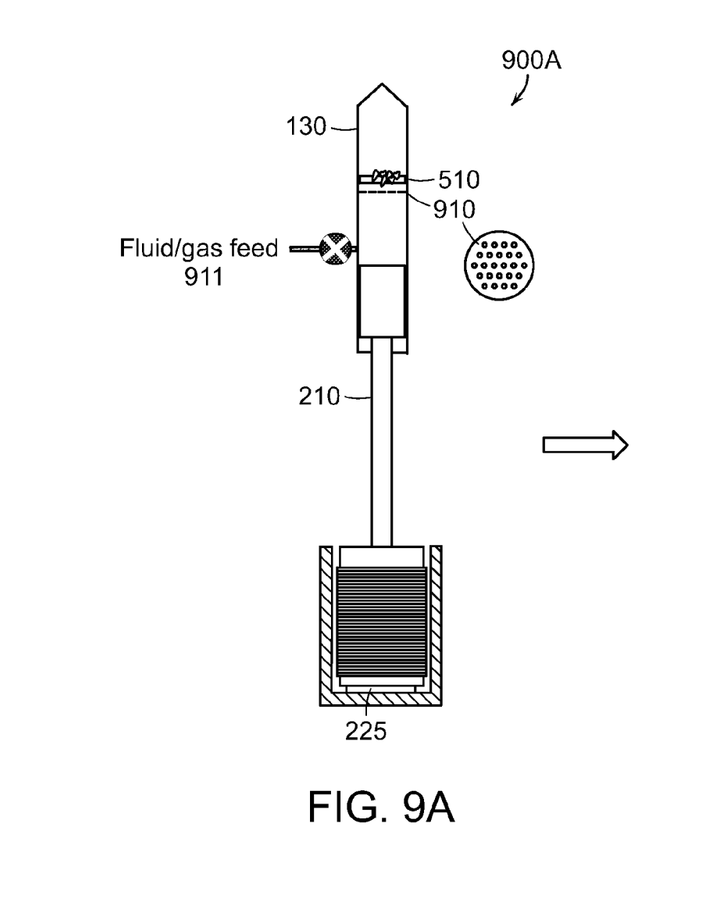
FIG. 9A-9B are schematics showing fluidization of solid particulate material according to an example embodiment.
Figure 9B:
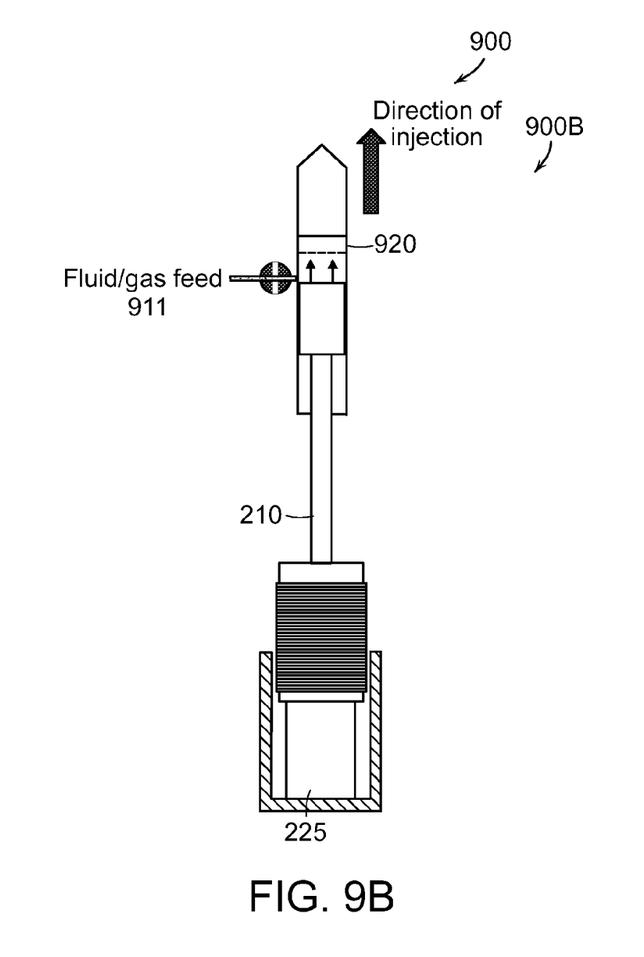

FIGS. 9A-9B are schematics 900A and 900B showing fluidization of solid particulate material (e.g., powdered drug 510) according to an example embodiment.

As shown in FIG. 9A, the solid particulate 510 is positioned in ampule 130 above a perforated plate 910. Actuation of the voice coil and by extension movement of the piston 210 in the forward direction, forces fluid (liquid or gas) 509 from a fluid/gas feed 911 up and through the solid particulate 510, increasing velocity causing the particles to reach a critical state where they are suspended within the fluid 509. This fluid-like behavior allows the contents 920 to be ejected through the nozzle orifice in the direction of injection 900 and into a biological body.

While this invention has been particularly shown and described with references to example embodiments thereof, it will be understood by those skilled in the art that various changes in form and details may be made therein without departing from the scope of the invention encompassed by the appended claims.

What is claimed is:

1. An apparatus for delivering a formulation to a biological body, the apparatus comprising:
   a first chamber for holding a powdered formulation;
   a bi-directional Lorentz-Force electromagnetic actuator in communication with the first chamber;
   a controller which during operation electrically controls the actuator, the controller being configured to cause the actuator to generate, when activated, a pressure within the first chamber to mix the powdered formulation and a diluent within the first chamber and to then oscillate contents of the first chamber to further mix the powdered formulation and the diluent in the first chamber in time for delivering into the biological body; and
   a needle-free injection nozzle in fluid communication with the first chamber, the nozzle being configured to enable the actuator to deliver the resulting mixture directly into the biological body as a jet that pierces a surface of the biological body.

2. The apparatus of claim 1 further including a second chamber for holding the diluent for mixing with the powdered formulation.

3. The apparatus of claim 2 further including at least one valve, the at least one valve including at least two ports, a first port coupled with the first chamber and a second port coupled with the second chamber for passing the diluent.

4. The apparatus of claim 1 wherein the controller, upon activation, is configured to cause the actuator to aspirate the diluent into the first chamber before causing the actuator to oscillate the contents of the first chamber.

5. The apparatus of claim 1 wherein the controller, upon activation, is configured to cause the actuator to aspirate the diluent from at least one of a medication vial or the biological body before causing the actuator to oscillate the contents of the first chamber.

6. The apparatus of claim 1 further including at least one valve, the at least one valve having a fluid path to a fluid source that upon being opened delivers the diluent for mixing with the powdered formulation.

7. The apparatus of claim 1 wherein the controller, upon activation, is configured to cause the actuator to deliver a mixture resulting from mixing of the powdered formulation and the diluent into the biological body.

8. The apparatus of claim 1 wherein the controller, upon activation, is configured to activate the actuator by using a preprogrammed waveform and is configured to cause the actuator to deliver the mixed formulation into the biological body.

9. The apparatus of claim 1 further including the diluent, and wherein the diluent is water or physiological saline.

10. The apparatus of claim 1 wherein the first chamber further holds the diluent, the powdered formulation and the diluent being separated by an air gap.

11. The apparatus of claim 10 further including a sensor that monitors displacement and volume of the powdered formulation and the diluent in relation to the air gap.

12. The apparatus of claim 1 further including a reservoir connected to the first chamber by at least one valve, the valve when opened allowing pressurized diluent to flow into the first chamber through the powdered formulation resulting in fluidization of the powered formulation in time for delivering into the biological body.

13. The apparatus of claim 12 wherein the diluent is gas.

14. The apparatus of claim 13 wherein the gas is hydrogen.

15. The apparatus of claim 1 wherein the diluent and the powdered formulation are configured to be mixed within the first chamber.

16. A method for delivering a formulation to a biological body, the method comprising:

maintaining a powdered formulation in a first chamber; and activating a bi-directional Lorentz-Force electromagnetic actuator to generate a pressure within the first chamber, the pressure resulting in mixing of the powdered formulation and a diluent in the first chamber;

oscillating contents of the first chamber with the actuator to further mix the powdered formulation and the diluent in the first chamber in time for delivering into the biological body; and delivering the resulting mixture directly into the biological body as a jet that pierces a surface of the biological body.

17. The method of claim 16 further including storing the diluent for mixing with the powdered formulation in a second chamber.

18. The method of claim 16 further including aspirating the diluent into the first chamber before oscillating the contents of the first chamber.

19. The method of claim 18 wherein the aspirating of the diluent is from at least one of a medication vial or the biological body.

20. The method of claim 16 wherein the activating of the actuator is accomplished by using a preprogrammed waveform.

21. The method of claim 16 wherein the diluent is water or physiological saline.

22. The method of claim 16 further including holding the diluent and the powdered formulation in the first chamber, the diluent and powdered formulation being separated by an air gap.

23. The method of claim 22 further including monitoring displacement and volume of the powdered formulation and the diluent in relation to the air gap.

24. The method of claim 22 further including purging air from the first chamber before delivering the resulting mixture.

25. The method of claim 16 further including fluidizing the powdered formulation as a function of directing pressurized diluent into the first chamber.

26. The method of claim 25 wherein the diluent is gas.

27. The method of claim 26 wherein the gas is hydrogen.

* * * * *